(12) United States Patent
Costantino

(10) Patent No.: US 8,063,770 B2
(45) Date of Patent: Nov. 22, 2011

(54) SYSTEM AND METHOD FOR FACIAL NERVE MONITORING

(76) Inventor: Peter Costantino, Armonk, NY (US)

( * ) Notice: Subject to any disclaimer, the term of this patent is extended or adjusted under 35 U.S.C. 154(b) by 827 days.

(21) Appl. No.: 11/854,967

(22) Filed: Sep. 13, 2007

(65) Prior Publication Data

US 2009/0033486 A1    Feb. 5, 2009

Related U.S. Application Data

(60) Provisional application No. 60/963,040, filed on Aug. 1, 2007.

(51) Int. Cl.
G08B 23/00     (2006.01)
A61B 5/00      (2006.01)
A61N 1/00      (2006.01)
A61M 31/00     (2006.01)

(52) U.S. Cl. ............... 340/539.12; 340/573.1; 600/300; 600/301; 607/62; 604/66

(58) Field of Classification Search .................... None
See application file for complete search history.

(56) References Cited

U.S. PATENT DOCUMENTS

| 6,025,129 | A  | * | 2/2000  | Nova et al. ................... 506/28 |
| 6,081,741 | A  | * | 6/2000  | Hollis .......................... 600/424 |
| 7,022,072 | B2 | * | 4/2006  | Fox et al. ..................... 600/365 |
| 7,272,433 | B2 | * | 9/2007  | Riff et al. ..................... 600/510 |
| 7,382,247 | B2 | * | 6/2008  | Welch et al. ............ 340/539.12 |
| 7,666,151 | B2 | * | 2/2010  | Sullivan et al. ............... 600/587 |
| 2003/0004554 | A1 | * | 1/2003 | Riff et al. .................... 607/62 |
| 2005/0027192 | A1 | * | 2/2005 | Govari et al. ................ 600/424 |
| 2008/0228238 | A1 | * | 9/2008 | Libbus .......................... 607/44 |
| 2008/0275349 | A1 | * | 11/2008| Halperin et al. ............ 600/484 |
| 2009/0054946 | A1 | * | 2/2009 | Sommer et al. ............... 607/28 |
| 2009/0088608 | A1 | * | 4/2009 | Mumford et al. ........... 600/300 |
| 2009/0157141 | A1 | * | 6/2009 | Chiao et al. .................. 607/46 |
| 2009/0231125 | A1 | * | 9/2009 | Baldus et al. ............ 340/539.12 |
| 2009/0264967 | A1 | * | 10/2009| Giftakis et al. .............. 607/62 |
| 2010/0036384 | A1 | * | 2/2010 | Gorek et al. ................. 606/104 |

* cited by examiner

Primary Examiner — Julie Lieu
(74) Attorney, Agent, or Firm — Handal & Morofsky, LLC

(57) ABSTRACT

In accordance with the invention apparatus is provided for monitoring the activity of a surgeon. The apparatus comprises a plurality of wireless sensing units for producing an output indicative of nerve stimulation. A receiver takes the output of the receiver units and produces at its output a plurality of signals each corresponding to the output of one of the plurality of wireless sensing units. An analyzer unit receives the plurality of signals each corresponding to the output of one of the plurality of wireless sensing units from the receiver. An indicator responds to the output of the analyzer unit.

26 Claims, 5 Drawing Sheets

SYSTEM AND METHOD FOR FACIAL NERVE MONITORING

RELATED APPLICATION

This application is a non-provisional application based on and claiming the priority of U.S. patent application Ser. No. 60/963,040.

FIELD OF THE INVENTION

The invention relates to the monitoring of nerve responses during surgery, and, in particular, the monitoring of facial nerves during surgery with the object of preventing permanent nerve damage.

BACKGROUND

In recent years, cosmetic surgery, and, in particular, cosmetic facial surgery is seeing dramatically increased use. This increase in the number of procedures performed each year is largely due to the fact that in the addition to the more elaborate and traditional face lift, other procedures, such as various versions of the S-lift are seeing widespread and increased performance. These procedures can be performed in one or two hours and require dramatically decreased recovery times. Moreover, such surgeries are often performed at relatively low-tech and small facilities, such as a doctor's office. Often such facilities specialize in that procedure only.

SUMMARY OF THE INVENTION

One potential complication in facial surgery is the possibility of doing damage to the facial nerves, which can result in paralysis of a portion of the face.

While equipment is available for monitoring the firing of a nerve, which can be detected (for example, by the twitching of a muscle) prior to the infliction of serious permanent injury, such systems are not using facial surgery because the wires connecting the nerve firing transducers interfere with the performance of the surgery. Accordingly, substantial numbers of individuals undergo facial surgery today and sometimes leave the operating table with permanent nerve injury.

In accordance with the invention apparatus is provided for monitoring the activity of a surgeon. The apparatus comprises a plurality of wireless sensing units for producing an output indicative of nerve stimulation. A receiver takes the output of the receiver units and produces at its output a plurality of signals each corresponding to the output of one of the plurality of wireless sensing units. An analyzer unit receives the plurality of signals each corresponding to the output of one of the plurality of wireless sensing units from the receiver. An indicator responds to the output of the analyzer unit.

The wireless sensing units may mechanically sense muscle movement. Alternatively, the wireless sensing units may comprise an inertial transducer.

The wireless sensing units may be powered by a battery or by induced electricity from an external electromagnetic field. The receiver is coupled to an antenna contained within a headrest cushion supporting the head of a patient being operated on. The wireless sensing units may be imprinted with an alphanumeric or other visual indicator which appears on a display unit associated with the receiver. The receiver may be coupled to a personal computer and the visual indicator may be the display of the personal computer.

The display of the personal computer may be a touchscreen, and control functions associated with the apparatus are implemented as touchably actuated icons on the touch screen. These functions may be varied and labeled in various ways by the computer. Moreover, the surgeon may select desired modes of display or labeling. In accordance with the invention, the display includes a plurality of individual displays, each of the individual displays being associated with one of the plurality of wireless sensing units. The individual displays many include an alphanumeric or other visual indicator which appears on a corresponding wireless sensing units. The individual displays may provide a meter-like indication of the amplitude of the signal produced by its respective wireless sensing units. The individual displays may change color in response to the amplitude of the signal produced by its respective wireless sensing unit.

The display may comprise a plurality of screen indicators which are positioned with respect to each other in a manner which mimics the position of the wireless position transducers. The position of the wireless sensors maybe detected by the receiver and the indicator may be the screen of a personal computer, in which the position of the indicators are arranged to mimic the position of their respective wireless position transducers.

Each of the wireless sensing units may be irreversibly programmed with an indication of a particular body portion or part or the like.

In accordance with the invention, the output of the receiver may be stored for later retrieval in association with an authenticating timestamp signal.

Alternatively, the wireless sensing units may output an analog or digital signal.

The indicator may be responsive to the analyzer to generate an alarm if a predetermined threshold is exceeded. The predetermined threshold may be a threshold in change in the output of a particular wireless sensing unit over a particular period of time. The predetermined threshold may be a threshold in change in the value of a particular wireless sensing unit.

The wireless position transducers may be associated with alphanumeric or other visual indicators which correspond to corresponding indicators on the screen indicators. The appearance of the indicator may include an alphanumeric or other indication of the position of the area where damage may be occurring.

The appearance or sound of the indicator may vary in a manner which signals the seriousness of the detected condition.

Optionally, the indicator outputs a normalized signal.

Optionally, the plurality of wireless sensing units are sequentially read.

It accordance with the invention, a wireless neurophysiologic monitoring/myophysiologic monitoring tack-shaped transducer/transmitter that, for example, senses muscle movement and then transmits that data to a receiver either during an operation, or in other diagnostic settings. It may be powered wirelessly via an electromagnetic field. Alternatively, a small wafer-like battery in the transducer/transmitter housing may also be used to power the unit. In most applications, such battery power would be appropriate as it is likely that the same will function for as long as a few hours.

In accordance with the invention, a re-usable, for example, "donut-shaped" (or U-shaped) cushioned headrest supports the head of the patient during surgery. A radio antenna contained within the headrest connected to a receiver senses the output of the transducer/transmitters due to nerve activity. This output which drives a personal computer or purpose built monitoring unit receives the output from the transducer/transmitters. Likewise, electrical components housed within the headrest may be used to power the transmitter/transducers.

This may be done with an electromagnetic field. The headrest (which is waterproof and can be gas sterilized) places the receiver within ten inches of the transducer/transmitter. A device placed nearby the patient or within the operating room for the receiver portion of the invention should also be contemplated.

The invention also contemplates the use of dissection instruments consisting of probes, dissecting forceps, dissecting scissors, etc. that can transmit a stimulating current, delivered to the nerve by the surgeon for purpose of locating nerves during surgery and confirming that they are either intact or damaged. The use of a milliamp stimulator "docking station" for a personal computer is contemplated in accordance with the invention. This allows the computer to control the milliamp output that his used to stimulate the nerve using the above various instruments. Additionally, a stimulator separate from the computer could be used for this purpose.

An electronic stimulator that generates a stimulating current may be integrated with the sensing computer in accordance with the invention for the purpose of stimulating the nerve to determine the ability of the transducer/transmitter to detect nerve firing and resulting movement. In accordance with the invention it is contemplated that the surgeon or technician will control the amplitude of such stimulation. It is further contemplated that this may be done under the control of the personal computer.

In accordance with the invention is contemplated that the transducer/transmitters will be disposable or reusable.

The transducer/transmitters may contain a microchip that allows them to be selectively programmed as to the site of the body or nerve that they will be monitoring. Likewise, transducer/transmitters may also be programmed or otherwise designed so that their electronic outputs are labeled separately from each other when sensed by the receiver/computer. A hand-held programming "pen" may be used at the time of transducer/transmitter placement. The transducer/transmitter may also be irreversibly programmed at manufacture so that it can only be used for a specific area of the body (i.e., the facial nerve).

The computer software has the capability of recording the EMG data from the patient, and is capable of generating an audible tone indicating nerve firing and possible nerve injury. The inventive system also contemplates recording the data from the entire operation so that it can be retrieved, and has a mechanism by which this data is tamper proof and time-stamped so that from a legal standpoint the data can be submitted in a court of law as evidence.

The monitoring computer is provided with a screen which may show data similar to that shown by existing nerve action monitoring equipment.

In accordance with the invention, it is contemplated that a personal computer, programmed with appropriate software, may be used to monitor and process data from the transducer/transmitters.

While the intended device and method is described in the context of monitoring the facial nerve, other types of neurophysiologic, neurosensory, and motor evoked response data is contemplated as part of this invention.

DESCRIPTION OF THE DRAWINGS

Several nonlimiting exemplary embodiments of the present invention are illustrated in the attached drawings, in which.

DETAILED DESCRIPTION OF THE PREFERRED EMBODIMENTS

Figure 1:
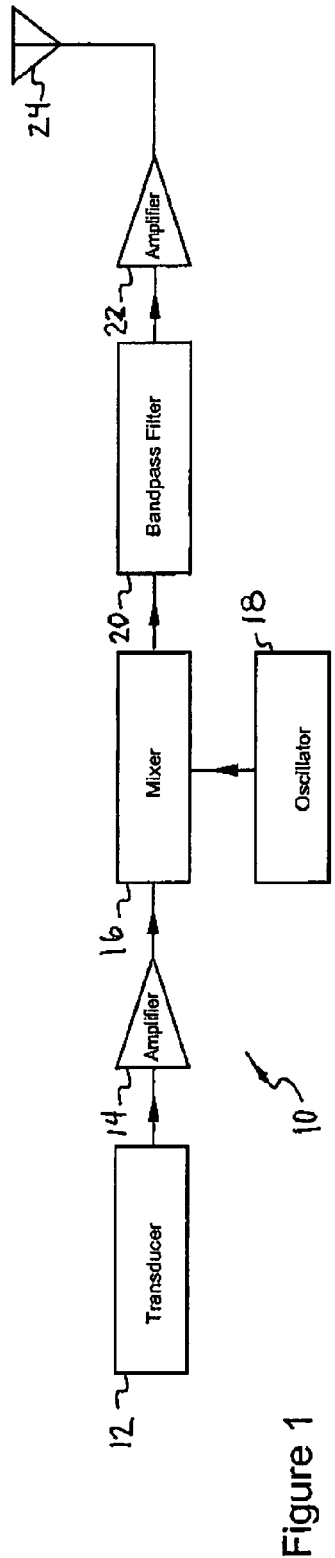
FIG. 1 is a block diagram of a nerve response transducer/transmitter constructed in accordance with the present invention.

Referring to FIG. 1, a transmitter/transducer 10 constructed in accordance with the present invention and useful in the practice of the method of the present invention is illustrated. Transmitter/transducer 10 comprises a transducer 12, of conventional design, which is adapted to detect firing of a nerve and produce an electrical output proportional to the amplitude of such firing. The same may be a movement detector such as an inertial detector, and the computer to which its output is sent, as detailed below, may have software to prevent the detection of a benign movement as a twitch signaling the onset of nerve damage. Alternatively, any other type of detector, such as electrodes similar to those used in electrocardiogram systems, may be used.

Thus, each transducer/transmitter may operate at its own unique carrier signal frequency.

The output of transducer 12 it is sent to an ample our forte in which amplifies a signal and sends it to a mixer 16 which acts as a modulator. Mixer 16 multiplies the output of amplifier 14 by the output of oscillator 18, forming an amplitude modulation signal with the carrier frequency equal to the frequency of oscillator 18. This amplitude modulated signal is sent to a bandpass filter 20, which removes unwanted modulation products. The filtered carrier signal with transducer information modulated onto it is then received by and amplified by amplifier 22 and output to antenna 24.

In accordance with the present invention, it is anticipated that a plurality of transducer/transmitters 10 will be placed on the face of a patient during surgery. Each of the transducer/transmitters 10 operates at a different carrier frequency, and, accordingly, transmits a separate identifiable and several the detectable signal indicating nerve function and, in particular, nerve firing.

These signals from a plurality of transducer/transmitters 10 may be picked up by an antenna 26 on a receiver 28. Receiver 28 comprises a tuned circuit 30 which receives the output of antenna 26 in a conventional fashion and provides its output to an RF amplifier 32. The output of RF amplifier 32 is sent to a mixer 34, which is driven by a heterodyne oscillator 36 to produce a plurality of heterodyne signals which are coupled to a plurality of signal buses 38-52, which while they each carry all heterodyne products, are each assigned to a particular heterodyne product. Heterodyne oscillator 36 operates at frequency $F_h$. Signal buses 38-52 are associated with heterodyne modulation products $F_h\text{-}F_1$, $F_h\text{-}F_2$, $F_h\text{-}F_3$, $F_h\text{-}F_4$, $F_h\text{-}F_5$, $F_h\text{-}F_6$, $F_h\text{-}F_7$, and $F_h\text{-}F_8$.

Buses 38-52 drive heterodyne product bandpass filters 54-68, respectively, which in turn drive detectors 70-84, respectively. The outputs of detectors 70-84, are provided to analog to digital converters 86100, respectively. The outputs of these analog-to-digital converters are provided to programmable digital logic circuit 102, which may be a microprocessor, personal computer, or any other suitable device.

In accordance with the invention, the outputs of a plurality of transducer/transmitters such as those illustrated in FIG. 1 are continuously monitored by programmable digital logic 102 to provide information respecting nerve firings. Such information may be of an analog nature and may be indicated with an analog display. Alternatively, alarms may be sounded if a dangerous condition is detected. In accordance with the present invention, it is also possible to combine, for example, one or more of such alarms as visible alarms, analog readouts, audible alarms, and so forth.

One potential monitoring device is console display 104. Display 104 may be a dedicated device with suitable display members and mechanical buttons. Alternatively, display 104 may be a liquid crystal display monitor typically associated with a personal computer. In accordance with a particularly preferred embodiment of the present invention, display 104 may be a computer monitor provided with a touchscreen feature which enables the actuation of icons by the finger of a user.

In accordance with the invention, display 104 is provided with a number of indicators 106-120. In accordance with preferred embodiment illustrated in FIG. 2, display 104 is a liquid crystal touchscreen display device of conventional design. Likewise, in accordance with the preferred embodiment of the invention, programmable digital logic 102 is a personal computer.

Indicators 106-120 include numerals 122 which identify the transducer with which they are associated. Likewise, in the event that there is an indication of an alarm condition, a display 125 indicates the location of the alarm condition. The same may also be accompanied by an audible alarm.

The amplitude of signal detection is shown by conventional bar graph indicator segments 124 which may have low or normal values as illustrated in four example, indicator 106 or high values as indicated by indicator 118. In addition, color coding may be used, for example indicator segments 124 may be green during normal operation, amber to signify a heightened alert condition, and red to indicate a dangerous condition. In accordance with the invention, it is contemplated that different audible cues will be associated with different levels of alert. For example, an amber heightened alert may be indicated by a beep, while a red dangerous condition may be indicated by a repetitive siren-like sound.

In accordance with the invention, it is contemplated that individual transmitters will be associated with a particular body part or portion of the face, for example. This may be done in a number of fashions. First the transmitter may be encoded to transmit a particular body portion identification. Alternatively, a particular use may be programmed. For example, a transducer with the number "1" printed on it may be placed by the physician and then "Select" icon 126 pushed until indicator 106 begins to blink. The surgeon or assistant would then push "Set" icon 128. The "Select" icon 126 may then be pushed repeatedly to close the sequential display of various face portion areas in display 125. Once the proper face portion appears in display 125, "Set" button 128 is depressed. Pressing "Select" button 126 then causes the next indicator 106-122 be selected.

It is also noted that, in accordance with the present invention, buttons for surgeon or surgeon's assistant may be made to change depending on their function, with the appropriate buttons being presented at the appropriate times. Such changing may be done in systems employing a liquid crystal display device or other display device having a touch screen.

Figure 3:
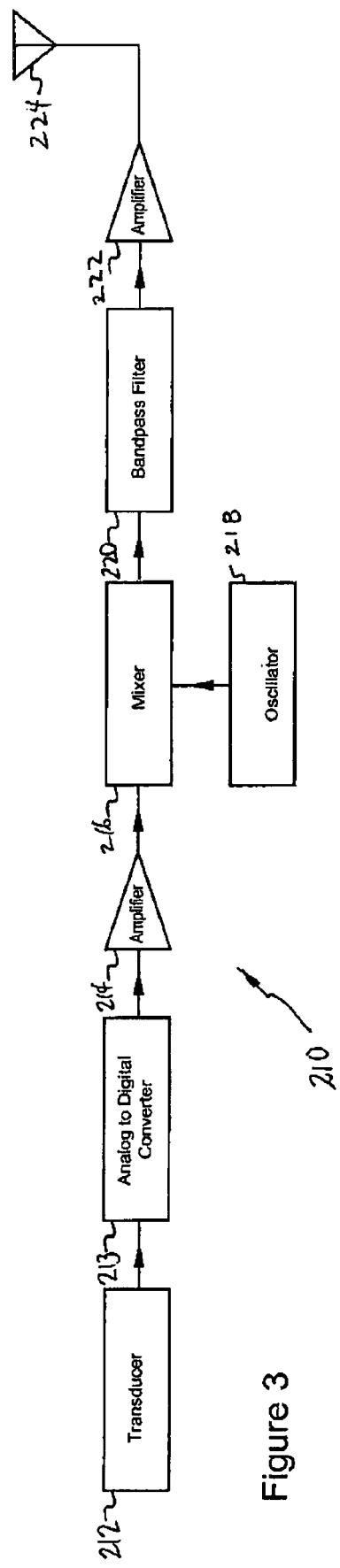
FIG. 3 is a block diagram of a transmitter similar to that of FIG. 1, except providing information in digital form.

Referring to FIG. 3, an alternative digital version of the transmitter/transducer 210 constructed in accordance with the present invention and useful in the practice of the method of the present invention is illustrated. Transmitter/transducer 210 comprises a transducer 212, of conventional design, which is adapted to detect firing of a nerve and produce an electrical output proportional to the amplitude of such firing.

The output of transducer 212 is sent to an analog to digital converter 213, which in turn, has its output sent to an amplifier 214 which amplifies the signal and sends it to a mixer 216 which acts as a modulator. Mixer 216 multiplies the output of amplifier 214 by the output of oscillator 218, forming an amplitude modulation signal with the carrier frequency equal to the frequency of oscillator 218. This amplitude modulated signal is sent to a bandpass filter 220, which removes unwanted modulation products. The filtered carrier signal with transducer information modulated onto it is then received by and amplified by amplifier 222 and output to antenna 224.

Frequency modulation may also be used.

The digital transducer/transmitter illustrated in FIG. 3 has the advantage of having a numerical output guy you at the receiver which is independent of the quality of the channel coupling the transmitter to the receiver. However, the receiver is of somewhat different design, as illustrated in FIG. 4 where similar or analogous components have been numbered with numbers 200 higher than those of the corresponding components in the embodiment of FIG. 2.

Figure 4:
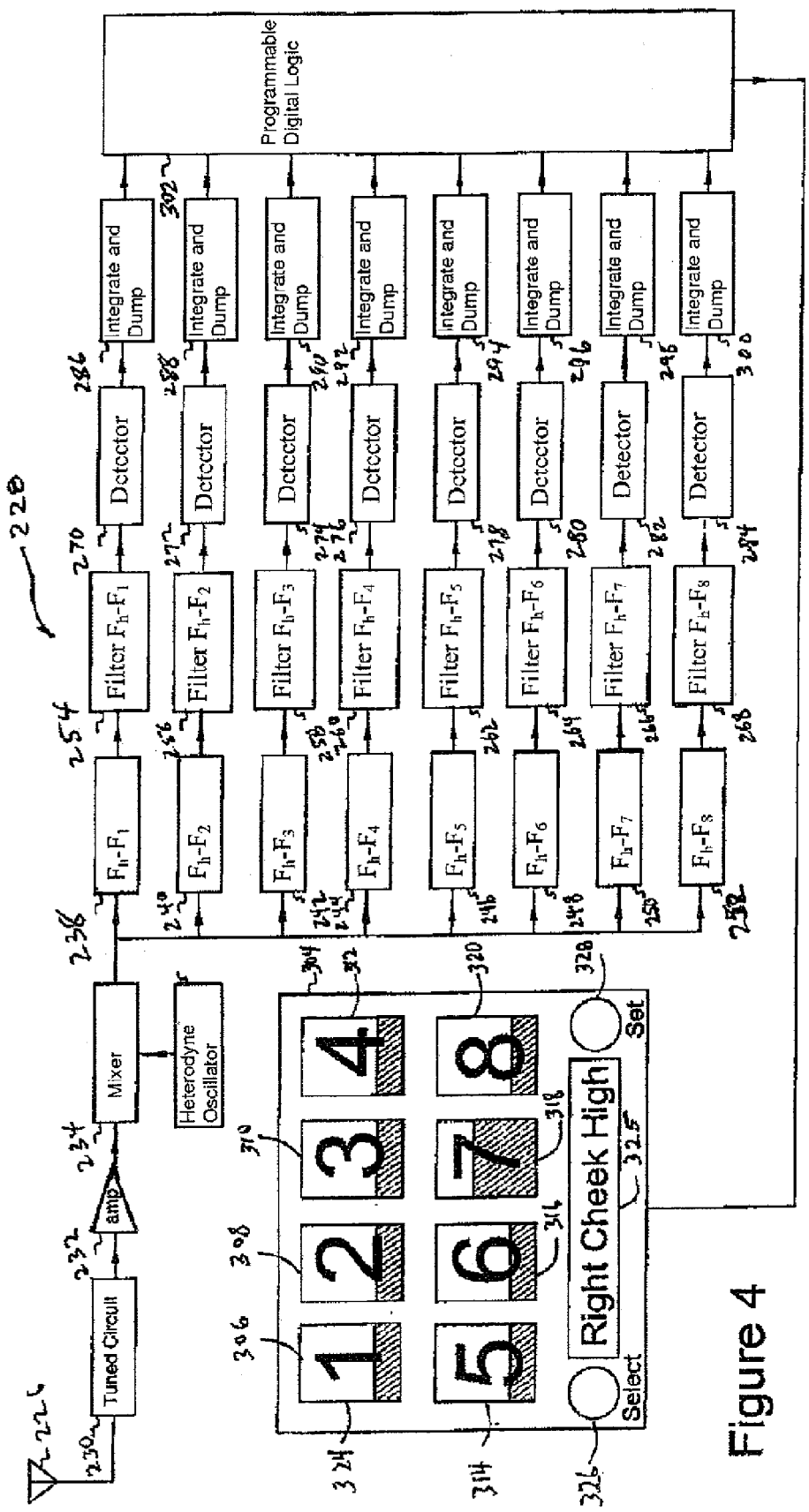
FIG. 4 is a block diagram of an alternative embodiment of the present invention useful in conjunction with the transmitter/transducer illustrated in FIG. 3.

The operation of receiver 228 illustrated in FIG. 4 is substantially identical to that of the receiver illustrated in FIG. 1, except that because the output of detectors 270-284 is already in digital form, there is no need to convert to a digital number. However, standard integrate and dump circuits 286-300 are provided to improve noise immunity.

Figure 5B:
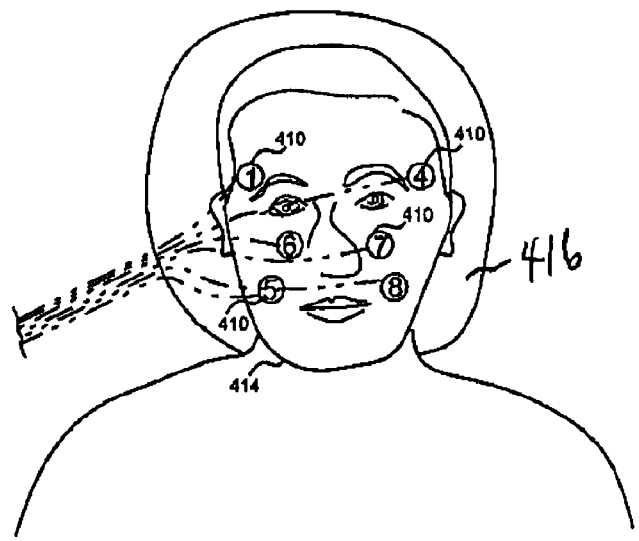
FIG. 5b is a view similar to FIG. 5a, but including wires.
Figure 5A:
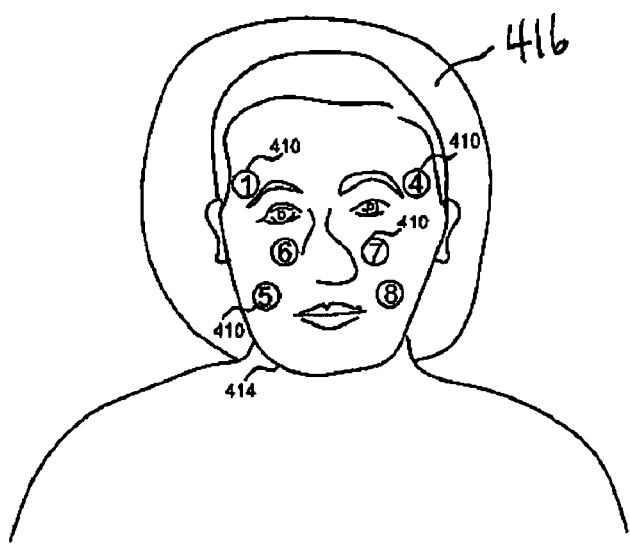
FIG. 5a shows a placement of the inventive transmitter/transducers on a facial surgery patient.

As illustrated in FIG. 5*a*, transducer/transmitters 410 may be placed at various portions on the face while taking up minimal space and not interfering with the performance of an operation. This would be in contrast to an arrangement in which wires 411 extending between transducers and a monitoring instrument would tend to block the area where the surgeon is working, as illustrated in phantom lines in FIG. 5*b*.

It accordance with the preferred embodiment, it is contemplated that transducer/transmitter units for 10 will be provided with, for example, suitable means of attachment comprising a layer of adhesive for a keen on their reverse sides, allowing them to be adhered to the skin on the face of the patient.

Figure 2:
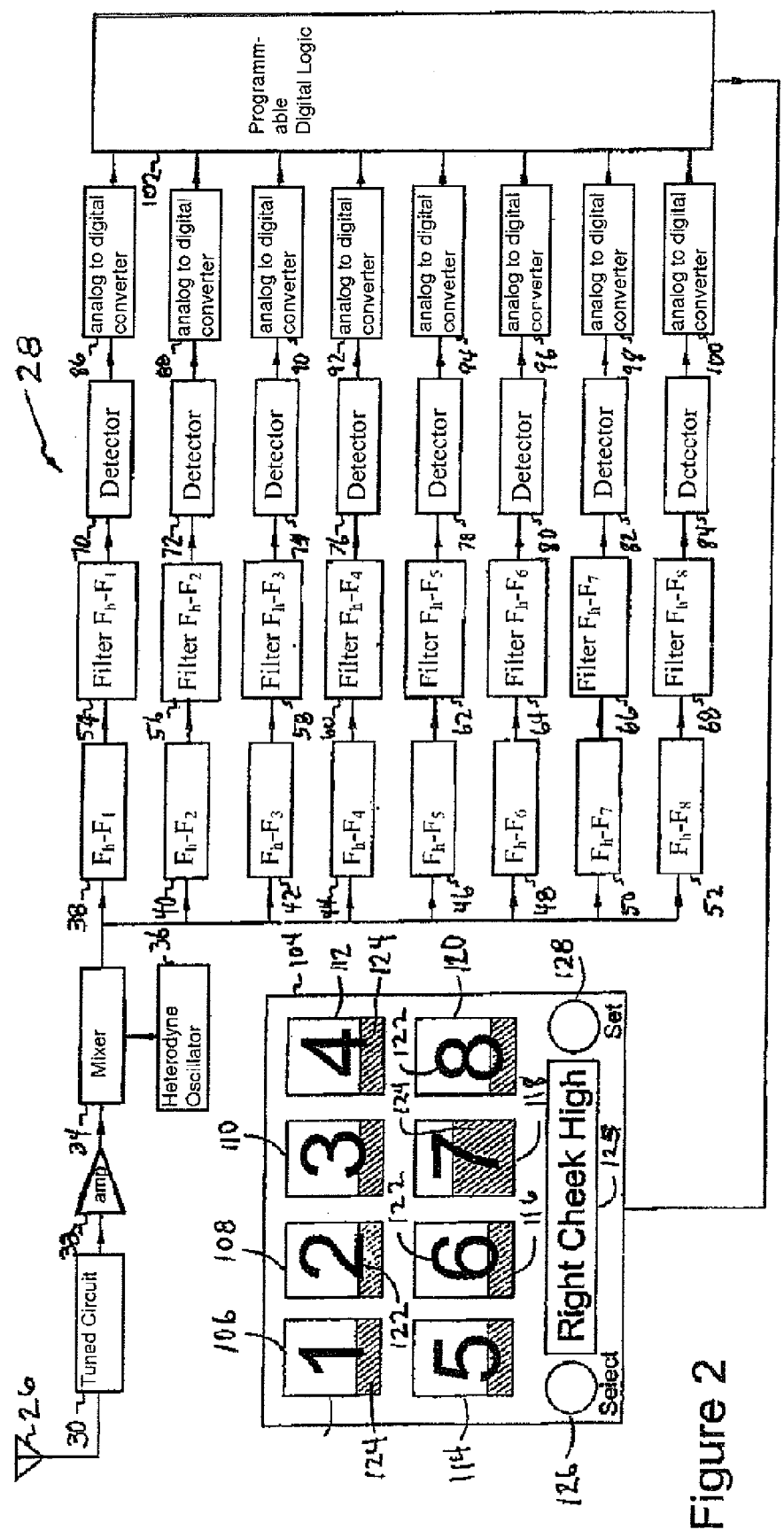
FIG. 2 is a block diagram of instrumentation for monitoring the output of the transmitter/transducer of FIG. 1.
Figure 6:
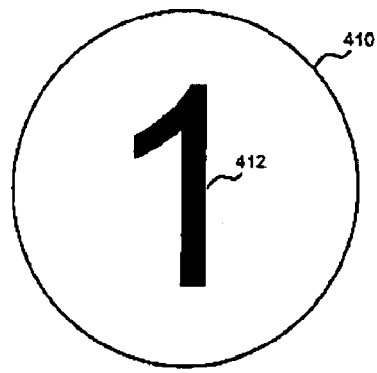
FIG. 6 is a top plan view of a transmitter/transducer constructed in accordance with the present invention and incorporating the circuitry of, for example, FIG. 1 or FIG. 2.
Figure 7:
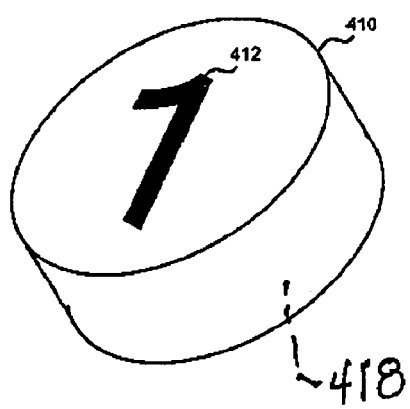
FIG. 7 is a perspective view of the transmitter/transducer of FIG. 6.

As alluded to above and as illustrated in FIGS. 6 and 7, in accordance with the present invention, individual transducer/transmitters 410 are provided with an alphanumeric indicator 412 corresponding to the alphanumerical indicators 122 in FIG. 2.

Transmitter/transducers 410 may be placed at various positions on the face 414 of a patient. Moreover, in accordance with the invention, the position of the transducers may be mimicked in the selection of receiver positions on the face of display 104. See, for example, the spatial relationship of the transducer numbers in FIG. 5 to the positions of the transducers in FIG. 2 or FIG. 4.

Antennas 26 and the radio receiver electronics may be housed in donut-shaped cushioned headset 416.

Figure 8:
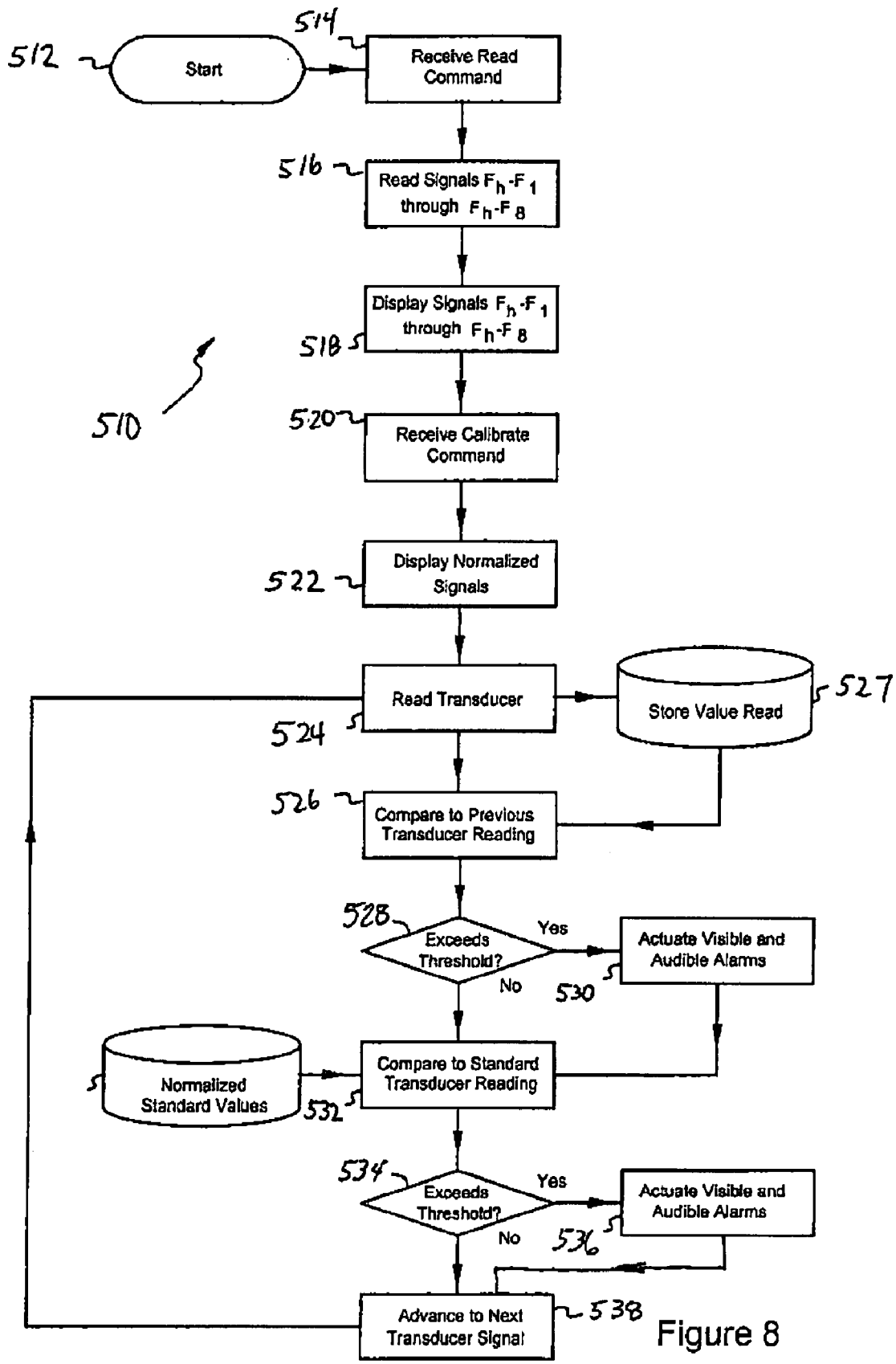
FIG. 8 is a flowchart illustrating the operation of the method of the present invention.

The inventive method of operation of the inventive systems is illustrated in FIG. 8. Method 510 begins with actuation of the system at step 512. Upon actuation, the system is ready to receive a read command at step 514. Upon the receipt of the read command, the system proceeds to read the signals output by the various transducer/transmitters placed by the surgeon on, for example, the face of the patient. The signals are read at step 516 and displayed at step 518.

At this point, the surgeon can look at the actual values being read by the transducers and determine whether the outputs are indicative of a good connection to the nerve. If a bad connection or faulty transducer/transmitter is detected, the transducer/transmitter may be reset, or replaced, as appropriate.

If desired, the surgeon has the option of normalizing the outputs of the transducers. For example such normalization may take the form of reducing the output of all transducers to zero or an appropriate low value. The surgeon may input a calibration command at step 520, causing the system to display the normalized signals on, for example, display 104 at step 522.

In accordance with the invention, the system is continuously and sequentially monitoring the outputs of all transducers/transmitters. Alternatively, such monitoring may be done simultaneously because of the frequency multiplexed nature of information transmission from individual nerves being monitored and receiver 28.

In accordance with the serial monitoring of transducer/transmitter outputs, a single transducer is read at step 524. The value of the output signal is sent to storage at step 527. The most recent value is then compared to the previous reading for that transducer at step 526 to determine potentially serious conditions. Such comparison is done by retrieving the previous value from memory. If the change in value exceeds a certain threshold, at step 528 the system proceeds to step 530 where, as appropriate, the desired visible and/or audible alarms are actuated. It accordance with the present invention, audible alarms or preferred as the surgeon need not look at the display.

The system then proceeds to step 532 where the detected value produced by the transducer is compared to a standard second threshold value believed to be indicative of a dangerous condition. Likewise, if the value detected at step 526 is not found to exceed a threshold at step 528, the system also proceeds to step 532. If the difference between the second standard value and the actual value exceeds the set threshold, at step 534 the system proceeds to step 536 to actuate, as desired, visible and/or audible alarms. After the actuation of the alarms at step 536 the system advances to the next transducer signal at step 538, as also occurs in the event that a determination is made that a threshold is not exceeded at step 534. The system then returns to step 524 to read the next transducer and determine whether a dangerous condition exist and or whether certain alarms are to be actuated.

What is claimed is:

1. Apparatus for monitoring the activity of a surgeon during a particular facial surgery procedure, comprising:
    (a) a plurality of wireless sensing units positioned at a plurality of points on the face of a patient being operated on, said points being positioned proximate to selected facial nerves, said selected facial nerves being at risk in said particular surgery, and said points being further positioned with respect to said nerves at risk, to be coupled to said nerves at risk, said wireless sensing units producing an output indicative of nerve stimulation and the magnitude of such stimulation;
    (b) a wireless receiver capable of receiving the output of said wireless sensing units and producing at its output a plurality of signals each corresponding to the output of one of said plurality of wireless sensing units;
    (c) an analyzer unit for receiving said plurality of signals each corresponding to the output of one of said plurality of wireless sensing units from said wireless receiver and comparing said plurality of signals to corresponding threshold values, said analyzer unit producing an alarm actuation output indicative of the existence of onset nerve reactions indicating the onset of nerve injury; and
    (d) an indicator responsive to said alarm actuation output of said analyzer unit to produce an alarm signal.

2. Apparatus as in claim 1, wherein said wireless sensing units are mechanically coupled to muscles associated with a nerve at risk and mechanically sense muscle movement by detecting the movement of said points on the face of the patient.

3. Apparatus as in claim 2, wherein said wireless sensing units comprise an inertial transducer.

4. Apparatus as in claim 1, wherein said wireless sensing units are powered by induced electricity from an external electromagnetic field.

5. Apparatus as in claim 1, further comprising a display associated with said wireless receiver, and wherein said wireless sensing units are imprinted with an alphanumeric or other visual indicator, said alphanumeric or other visual indicator appearing on said display unit associated with said wireless receiver.

6. Apparatus as in claim 5, wherein said display includes a plurality of individual displays, each of said individual displays being associated with one of said plurality of wireless sensing units.

7. Apparatus as in claim 1, wherein the output of said wireless receiver is stored for later retrieval in association with an authenticating timestamp signal.

8. Apparatus as in claim 1, wherein said indicator is a display comprising a plurality of individual display elements, each of said individual display elements associated with a wireless sensing unit, each said individual display elements providing a meter-like indication of the amplitude of the signal produced by its respective wireless sensing units.

9. Apparatus as in claim 8, wherein said individual display elements each change color in response to the amplitude of the signal produced by its respective wireless sensing unit.

10. Apparatus as in claim 9, wherein said indicator includes an alphanumeric or other indication of the position of the area where damage may be occurring.

11. Apparatus as in claim 1, wherein said indicator is responsive to said analyzer to generate an alarm if a predetermined threshold is exceeded.

12. Apparatus as in claim 11, wherein said predetermined threshold is a threshold in change in the output of a particular wireless sensing unit over a particular period of time.

13. Apparatus as in claim 11, wherein said predetermined threshold is a threshold in change in the value of a particular wireless sensing unit.

14. Apparatus as in claim 1, wherein said indicator comprises a plurality of screen indicators which are positioned with respect to each other in a manner which mimics the position of the wireless sensing units.

15. Apparatus as in claim 14, wherein said position is detected by said receiver and said indicator is the screen of a personal computer, in which the position of said indicators are arranged by the computer to mimic the position of their respective wireless sensing units.

16. Apparatus as in claim 15, wherein said wireless sensing units are associated with alphanumeric or other visual indicators which correspond to corresponding indicators on said screen indicators.

17. Apparatus as in claim 1, wherein said indicator includes an alphanumeric or other indication of the position of the area where damage may be occurring.

18. Apparatus as in claim 1, wherein said indicator varies in a manner which signals the seriousness of the detected condition.

19. Apparatus as in claim 1, wherein said indicator outputs a normalized signal.

20. A method for monitoring the activity of a surgeon performing a particular facial surgery procedure, comprising:
   (a) placing a plurality of wireless sensing units on the face of a facial surgery patient being operated, said sensing units being placed on at a plurality of points on the face of said patient to generate a plurality of signals, said points being positioned proximate to selected facial nerves, said selected facial nerves being at risk in said particular surgery, and said points being further positioned with respect to said nerves at risk, to be coupled to said nerves at risk;
   (b) producing an output indicative of nerve stimulation and the magnitude of such stimulation;
   (c) wirelessly transmitting said output indicative of nerve stimulation and the magnitude of such stimulation;
   (d) receiving the wirelessly transmitted output indicative of nerve stimulation and the magnitude of such stimulation at a receiver having a receiver output;
   (e) monitoring the output of said receiver;
   (f) analyzing said receiver output corresponding to the output of said plurality of wireless sensing units and comparing said plurality of signals to corresponding threshold values, said analyzer unit producing an alarm actuation output indicative of the existence of onset nerve reactions indicating the onset of nerve injury;
   (g) generating an alarm signal in response to the detection of said onset nerve reactions indicating the onset of nerve injury.

21. Apparatus as in claim 1, wherein said analyzer discriminates between a benign reaction of one of said nerves at risk and a nerve firing indicating the onset of nerve injury.

22. Apparatus as in claim 21, wherein said analyzer unit is responsive to a threshold value set by test stimulation and observation.

23. Apparatus as in claim 21, wherein said analyzer unit is responsive to a threshold value set by stimulation of a nerve at risk to determine the ability of a wireless sensing unit to detect nerve firing and resulting movement.

24. A method as in claim 20 further comprising performing a facial surgery during said monitoring of the output of said receiver.

25. Apparatus as in claim 1, wherein said wireless sensing units are RF units.

26. Apparatus for monitoring the activity of a surgeon, comprising:
   (a) a plurality of wireless sensing units for producing an output indicative of nerve stimulation;
   (b) a receiver capable of receiving the output of said wireless sensing units and producing at its output a plurality of signals each corresponding to the output of one of said plurality of wireless sensing units;
   (c) an analyzer unit for receiving said plurality of signals each corresponding to the output of one of said plurality of wireless sensing units from said receiver;
   (d) an indicator responsive to the output of said analyzer unit, wherein said receiver is coupled to an antenna contained within a headrest cushion supporting the head of a patient being operated on.

* * * * *